United States Patent
Walker et al.

(10) Patent No.: US 10,578,094 B2
(45) Date of Patent: Mar. 3, 2020

(54) PUMP FOR OPERATION IN RADIOACTIVE ENVIRONMENT

(71) Applicant: Curium US LLC, St. Louis, MO (US)

(72) Inventors: Martin R. Walker, O'Fallon, IL (US); Ryan W. Lenger, Brighton, IL (US); Kevin B. Graves, Catawissa, MO (US); Bryan S. Petrofsky, St. Louis, MO (US)

(73) Assignee: Curium US LLC, St. Louis, MO (US)

( * ) Notice: Subject to any disclaimer, the term of this patent is extended or adjusted under 35 U.S.C. 154(b) by 409 days.

(21) Appl. No.: 15/394,272

(22) Filed: Dec. 29, 2016

(65) Prior Publication Data
US 2017/0319778 A1    Nov. 9, 2017

Related U.S. Application Data

(60) Provisional application No. 62/331,651, filed on May 4, 2016.

(51) Int. Cl.
*F04B 43/12* (2006.01)
*F04B 43/09* (2006.01)
(Continued)

(52) U.S. Cl.
CPC .............. *F04B 43/12* (2013.01); *F04B 13/00* (2013.01); *F04B 43/09* (2013.01);
(Continued)

(58) Field of Classification Search
CPC ... F04B 43/12–43/1292; F04B 43/1253; F04B 43/1238
See application file for complete search history.

(56) References Cited

U.S. PATENT DOCUMENTS

| 3,128,716 A | 4/1964 | Stallman et al. |
| 3,179,634 A | 4/1965 | Edwards |
| (Continued) | | |

FOREIGN PATENT DOCUMENTS

| JP | H0669899 U | 9/1994 |
| JP | 2006349649 | * 12/2006 |
| (Continued) | | |

OTHER PUBLICATIONS

JP2006349649 English Translation, from EPO website. (Year: 2006).*

(Continued)

*Primary Examiner* — Bryan M Lettman
(74) *Attorney, Agent, or Firm* — Armstrong Teasdale LLP

(57) ABSTRACT

A system for manufacturing radionuclide generators includes an enclosure defining a radioactive environment. The enclosure includes radiation shielding to prevent radiation within the radioactive environment from moving to an exterior of the enclosure. The system also includes a pump within the enclosure for transferring fluid through tubing. The pump includes a pump head including a casing, a rotor that rotates in relation to the casing, and a clamp. The tubing extends through the pump head. The clamp compresses the tubing against the rotor and directs radioactive fluid through the tubing as the rotor rotates. The pump also includes a servomotor that controls the rotation of the rotor and a coupling connecting the pump head to the servomotor. The coupling prevents backlash between the servomotor and the rotor during rotation.

20 Claims, 10 Drawing Sheets

(51) Int. Cl.
    *F04B 13/00* (2006.01)
    *G21F 7/06* (2006.01)
    *A61M 5/00* (2006.01)
    *G21G 1/00* (2006.01)

(52) U.S. Cl.
    CPC ...... *F04B 43/1261* (2013.01); *F04B 43/1284* (2013.01); *G21F 7/06* (2013.01); *A61M 5/007* (2013.01); *G21G 1/0005* (2013.01)

(56) References Cited

U.S. PATENT DOCUMENTS

| | | | |
|---|---|---|---|
| 3,356,648 A | 12/1967 | Rogers | |
| 3,503,690 A | 3/1970 | Sciammarella | |
| 3,757,846 A | 9/1973 | Herman, Jr. | |
| 3,789,217 A | 1/1974 | Youmans | |
| 3,985,145 A | 10/1976 | Broscheit et al. | |
| 4,015,366 A | 4/1977 | Hall, III | |
| 4,066,590 A | 1/1978 | Eldred et al. | |
| 4,340,030 A | 7/1982 | Molivadas | |
| RE31,023 E | 9/1982 | Hall, III | |
| 4,387,704 A | 6/1983 | Minden | |
| 4,432,707 A | 2/1984 | Anderson et al. | |
| 4,451,750 A | 5/1984 | Heuer et al. | |
| 4,580,952 A * | 4/1986 | Eberle | F04B 47/04 417/383 |
| 4,642,988 A | 2/1987 | Benson | |
| 4,745,749 A | 5/1988 | Benson | |
| 4,868,843 A | 9/1989 | Nunan | |
| 4,868,844 A | 9/1989 | Nunan | |
| 5,146,086 A | 9/1992 | De et al. | |
| 5,731,567 A | 3/1998 | Kato et al. | |
| 5,814,909 A | 9/1998 | Yamada et al. | |
| 6,529,268 B1 | 3/2003 | Oka et al. | |
| 6,576,341 B1 | 6/2003 | Davey et al. | |
| 6,609,900 B2 * | 8/2003 | Lucke | F04B 43/0081 417/474 |
| 6,629,469 B2 | 10/2003 | Jaszczak et al. | |
| 6,736,617 B2 | 5/2004 | Domroese | |
| 6,737,770 B2 | 5/2004 | Sunaga et al. | |
| 7,330,242 B2 | 2/2008 | Reichert et al. | |
| 7,455,967 B2 | 11/2008 | Muller | |
| 7,642,450 B2 | 1/2010 | Connor | |
| 7,760,977 B2 | 7/2010 | Curdt et al. | |
| 7,956,108 B2 | 6/2011 | Coleman et al. | |
| 8,653,371 B2 | 2/2014 | Kibe et al. | |
| 8,684,513 B2 | 4/2014 | Tsunoya | |
| 8,696,543 B2 | 4/2014 | Forsell | |
| 9,169,422 B2 | 10/2015 | O'Hare et al. | |
| 2002/0093259 A1 | 7/2002 | Sunaga et al. | |
| 2003/0077396 A1 | 4/2003 | Lecompte et al. | |
| 2004/0036188 A1 | 2/2004 | Arboix et al. | |
| 2004/0051190 A1 | 3/2004 | Slack et al. | |
| 2004/0053327 A1 | 3/2004 | Muller | |
| 2004/0262795 A1 | 12/2004 | Slack et al. | |
| 2005/0288813 A1 | 12/2005 | Yang et al. | |
| 2006/0077865 A1 | 4/2006 | Eytan et al. | |
| 2006/0257999 A1 | 11/2006 | Chang et al. | |
| 2006/0260605 A1 | 11/2006 | Connor | |
| 2007/0058154 A1 | 3/2007 | Reichert et al. | |
| 2007/0059184 A1 | 3/2007 | Bach | |
| 2009/0042281 A1 | 2/2009 | Chang et al. | |
| 2009/0067792 A1 | 3/2009 | Curdt et al. | |
| 2009/0142846 A1 | 6/2009 | Crenshaw et al. | |
| 2009/0240100 A1 | 9/2009 | Forsell | |
| 2009/0240294 A1 | 9/2009 | Forsell | |
| 2009/0247817 A1 | 10/2009 | Forsell | |
| 2009/0248033 A1 | 10/2009 | Forsell | |
| 2009/0250068 A1 | 10/2009 | Forsell | |
| 2009/0254106 A1 | 10/2009 | Forsell | |
| 2010/0304136 A1 | 12/2010 | Coleman et al. | |
| 2011/0087337 A1 | 4/2011 | Forsell | |
| 2012/0200652 A1 | 8/2012 | Tsunoya | |
| 2012/0209341 A1 | 8/2012 | Forsell | |
| 2013/0259456 A1 | 10/2013 | Viswanathan | |
| 2014/0178513 A1 | 6/2014 | Matthews | |
| 2014/0234553 A1 | 8/2014 | O'Hare et al. | |
| 2015/0349694 A1 | 12/2015 | Feng et al. | |

FOREIGN PATENT DOCUMENTS

| | | |
|---|---|---|
| JP | 2006349649 A | 12/2006 |
| JP | 2007270689 A | 10/2007 |

OTHER PUBLICATIONS

International Search Report and Written Opinion of the International Searching Authority regarding PCT/US2016/069409 dated Apr. 10, 2017; pp. 13.

\* cited by examiner

PUMP FOR OPERATION IN RADIOACTIVE ENVIRONMENT

CROSS-REFERENCE TO RELATED APPLICATIONS

This application claims priority to U.S. Provisional Patent Application Ser. No. 62/331,651, filed May 4, 2016, the disclosure of which is hereby incorporated by reference in its entirety.

FIELD

The field of the disclosure relates generally to liquid handling systems and, more particularly, to a pump for operation in a radioactive environment.

BACKGROUND

Radioactive material is used in nuclear medicine for diagnostic and therapeutic purposes by injecting a patient with a small dose of the radioactive material, which concentrates in certain organs or regions of the patient. Radioactive materials typically used for nuclear medicine include Germanium-68 ("Ge-68"), Strontium-87m, Technetium-99m ("Tc-99m"), Indium-111m ("In-111"), Iodine-131 ("I-131") and Thallium-201. Such radioactive materials may be produced using a radionuclide generator. Radionuclide generators generally include a column that has media for retaining a long-lived parent radionuclide that spontaneously decays into a daughter radionuclide that has a relatively short half-life. The column may be incorporated into a column assembly that has a needle-like outlet port that receives an evacuated vial to draw saline or other eluant liquid, provided to a needle-like inlet port, through a flow path of the column assembly, including the column itself. This liquid may elute and deliver daughter radionuclide from the column and to the evacuated vial for subsequent use in nuclear medical imaging applications, among other uses.

During assembly of the radionuclide generators, radioactive materials may be formulated from a raw, concentrated form into a form having a desired concentration. For example, radioactive liquids may be homogeneously mixed, pH-adjusted, sampled, diluted, and dispensed. In addition, the radioactive liquids may be transferred between containers.

Accordingly, a need exists for a liquid handling system that accurately and precisely dispenses liquids and is suitable for use with radioactive materials.

This Background section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF SUMMARY

In one aspect, a system for manufacturing radionuclide generators is provided. The system includes an enclosure defining a radioactive environment. The enclosure includes radiation shielding to prevent radiation within the radioactive environment from moving to an exterior of the enclosure. The system also includes a pump within the enclosure for transferring fluid through tubing. The pump includes a pump head including a casing, a rotor that rotates in relation to the casing, and a clamp. The tubing extends through the pump head. The clamp compresses the tubing against the rotor and directs radioactive fluid through the tubing as the rotor rotates. The pump also includes a servomotor that controls the rotation of the rotor and a coupling connecting the pump head to the servomotor. The coupling prevents backlash between the servomotor and the rotor during rotation.

In another aspect, a pump for transferring fluid through tubing in a radioactive environment is provided. The pump includes a pump head including a casing, a rotor that rotates in relation to the casing, and a clamp. The tubing extends through the pump head. The clamp compresses the tubing against the rotor and directs radioactive fluid through the tubing as the rotor rotates. The rotor including a keyed shaft. The pump also includes a servomotor that controls the rotation of the rotor and includes a resolver to generate signals relating to the rotation of the rotor. The pump further includes a coupling connecting the pump head to the servomotor. The coupling is connected to the keyed shaft to prevent backlash between the servomotor and the rotor during rotation.

In yet another aspect, a method of transferring fluid through tubing in a radioactive environment is provided. The tubing extends through a pump head of a pump. The pump includes a casing, a rotor that rotates in relation to the casing, and a clamp. The method includes compressing the tubing against the rotor and rotating the rotor to direct fluid through the tubing. The rotor includes a keyed shaft. The method also includes controlling rotation of the rotor using a servomotor connected to the rotor by the keyed shaft and a coupling. The method further includes engaging the coupling and the keyed shaft to prevent backlash between the servomotor and the rotor during rotation.

Various refinements exist of the features noted in relation to the above-mentioned aspects. Further features may also be incorporated in the above-mentioned aspects as well. These refinements and additional features may exist individually or in any combination. For instance, various features discussed below in relation to any of the illustrated embodiments may be incorporated into any of the above-described aspects, alone or in any combination.

DETAILED DESCRIPTION

Figure 1:
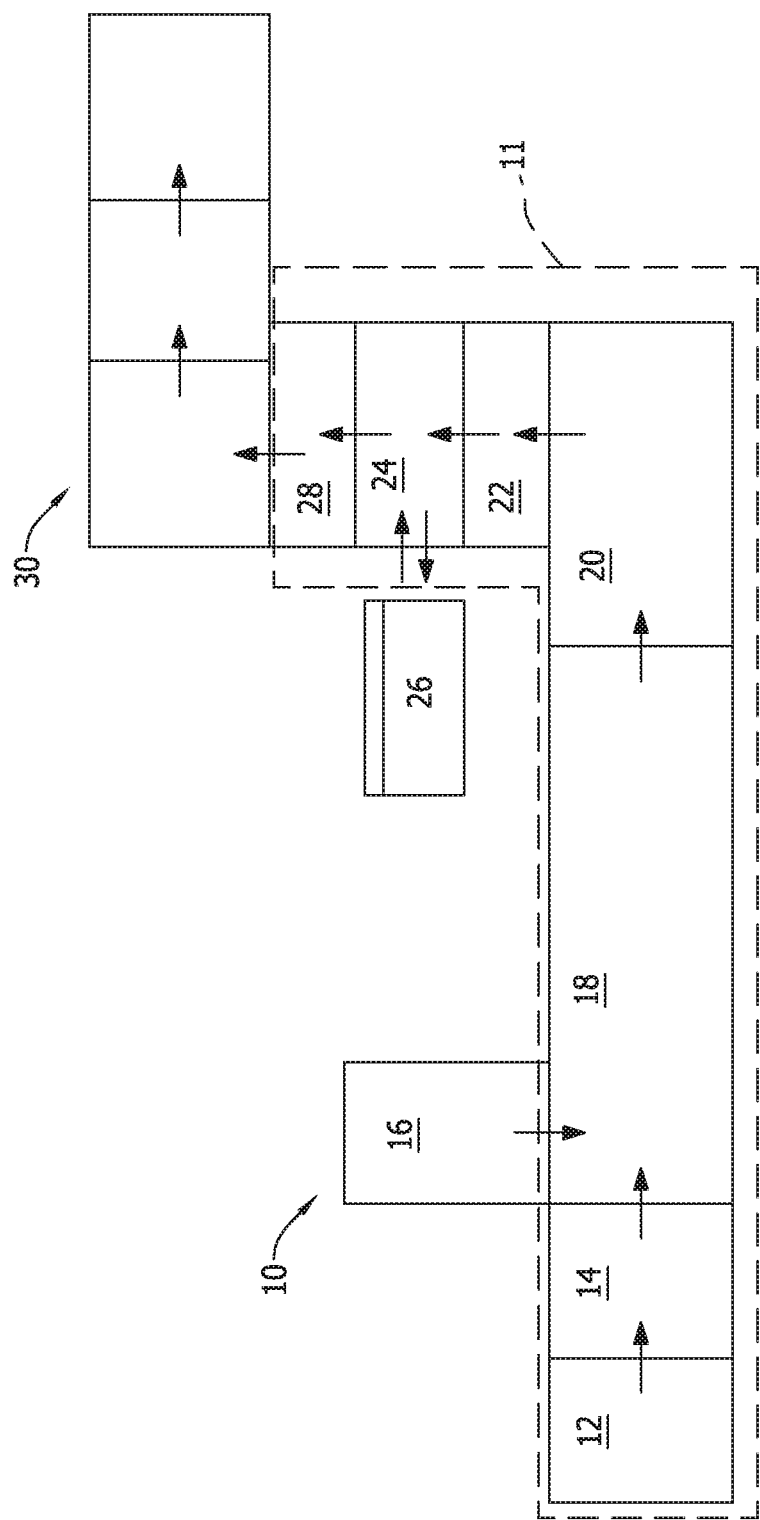
FIG. 1 is a schematic view of a system for producing radionuclide generators.

FIG. 1 is a schematic view of a system 10 for manufacturing radionuclide generators. The system 10 shown in FIG. 1 may be used to produce various radionuclide generators, including, for example and without limitation, Technetium generators, Indium generators, and Strontium generators. The system 10 of FIG. 1 is particularly suited for producing Technetium generators. A Technetium generator is a pharmaceutical drug and device used to create sterile injectable solutions containing Tc-99m, an agent used in diagnostic imaging with a relatively short 6 hour radiological half-life, allowing the Tc-99m to be relatively quickly eliminated from human tissue. Tc-99m is "generated" via the natural decay of Molybdenum ("Mo-99"), which has a 66 hour half-life, which is desirable because it gives the generator a relatively long two week shelf life. During generator operation (i.e., elution with a saline solution), Mo-99 remains chemically bound to a core alumina bed (i.e., a retaining media) packed within the generator column, while Tc-99m washes free into an elution vial, ready for injection into a patient. While the system 10 is described herein with reference to Technetium generators, it is understood that the system 10 may be used to produce radionuclide generators other than Technetium generators.

As shown in FIG. 1, the system 10 generally includes a plurality of stations or cells. In the example embodiment, the system 10 includes a cask loading station 12, a formulation station 14, an activation station 16, a fill/wash station 18, an assay/autoclave loading station 20, an autoclave station ("Autoclaves") 22, an autoclave unloading station 24, a quality control testing station 26, a shielding station 28, and a packaging station 30.

The cask loading station 12 is configured to receive and handle casks or containers of radioactive material, such as a parent radionuclide, and transfer the radioactive material to the formulation station 14. Radioactive material may be transported in secondary containment vessels and flasks that need to be removed from an outer cask prior to formulation. The cask loading station 12 includes suitable tooling and mechanisms to extract secondary containment vessels and flasks from outer casks, as well as to transfer flasks to the formulation cell. Suitable devices that may be used in the cask loading station include, for example and without limitation, telemanipulators.

At the formulation station 14, the raw radioactive material (i.e., Mo-99) is quality control tested, chemically treated if necessary, and then pH adjusted while diluting the raw radioactive material to a desired final target concentration. The formulated radioactive material is stored in a suitable containment vessel (e.g., within the formulation station 14).

Column assemblies containing a column of retaining media (e.g., alumina) are activated at the activation station 16 to facilitate binding of the formulated radioactive material with the retaining media. In some embodiments, column assemblies are activated by eluting the column assemblies with a suitable volume of hydrogen chloride (HCl) at a suitable pH level. Column assemblies are held for a minimum wait time prior to charging the column assemblies with the parent radionuclide.

Following activation, column assemblies are loaded into the fill/wash station 18 using a suitable transfer mechanism (e.g., transfer drawer). Each column assembly is then charged with parent radionuclide by eluting formulated radioactive solution (e.g., Mo-99) from the formulation station 14 through individual column assemblies using suitable liquid handling systems (e.g., pumps, valves, etc.). The volume of formulated radioactive solution eluted through each column assembly is based on the desired curie (Ci) activity for the corresponding column assembly. The volume eluted through each column assembly is equivalent to the total Ci activity identified at the time of calibration for the column assembly. For example, if a volume of formulated Mo-99 required to make a 1.0 Ci Generator (at time of calibration) is 'X', the volume required to make a 19.0 Ci Generator is simply 19 times X. After a minimum wait time, the charged column assemblies are eluted with a suitable volume and concentration of acetic acid, followed by an elution with a suitable volume and concentration of saline to "wash" the column assemblies. Column assemblies are held for a minimum wait time before performing assays on the column assemblies.

The charged and washed column assemblies are then transferred to the assay/autoclave load station 20, in which assays are taken from each column assembly to check the amount of parent and daughter radionuclide produced during elution. Each column assembly is eluted with a suitable volume of saline, and the resulting solution is assayed to check the parent and daughter radionuclide levels in the assay. Where the radioactive material is Mo-99, the elutions are assayed for both Tc-99m and Mo-99. Column assemblies having a daughter radionuclide (e.g., Tc-99m) assay falling outside an acceptable range calculation are rejected. Column assemblies having a parent radionuclide (e.g., Mo-99) breakthrough exceeding a maximum acceptable limit are also rejected.

Following the assay process, tip caps are applied to the outlet port and the fill port of the column assembly. Column assemblies may be provided with tip caps already applied to the inlet port. If the column assembly is not provided with a tip cap pre-applied to the inlet port, a tip cap may be applied prior to, subsequent to, or concurrently with tip caps being applied to the outlet port and the fill port. Assayed, tip-capped column assemblies are then loaded into an autoclave sterilizer located in the autoclave station for terminal sterilization. The sealed column assemblies are subjected to an autoclave sterilization process within the autoclave station to produce terminally-sterilized column assemblies.

Following the autoclave sterilization cycle, column assemblies are unloaded from the autoclave station into the autoclave unloading station 24. Column assemblies are then transferred to the shielding station 28 for shielding.

Some of the column assemblies are transferred to the quality control testing station 26 for quality control. In the example embodiment, the quality control testing station 26 includes a QC testing isolator that is sanitized prior to QC testing, and maintained at a positive pressure and a Grade A clean room environment to minimize possible sources of contamination. Column assemblies are aseptically eluted for in-process QC sampling, and subjected to sterility testing within the isolator of the quality control testing station 26. New tip caps are applied to the inlet and outlet needles of the column assemblies before the column assemblies are transferred back to the autoclave unloading station 24.

The system 10 includes a suitable transfer mechanism for transferring column assemblies from the autoclave unloading station 24 (which is maintained at a negative pressure differential, Grade B clean room environment) to the isolator of the quality control testing station 26. In some embodiments, column assemblies subjected to quality control testing may be transferred from the quality control testing station 26 back to the autoclave unloading station 24, and can be re-sterilized and re-tested, or re-sterilized and packaged for shipment. In other embodiments, column assemblies are discarded after being subjected to QC testing.

In the shielding station 28, column assemblies from the autoclave unloading station 24 are visually inspected for container closure part presence, and then placed within a radiation-shielding container (e.g., a lead plug). The radiation shielding container is inserted into an appropriate safe constructed of suitable radiation shielding material (e.g., lead, tungsten or depleted uranium). Shielded column assemblies are then released from the shielding station 28.

In the packaging station 30, shielded column assemblies from the shielding station 28 are placed in buckets pre-labeled with appropriate regulatory (e.g., FDA) labels. A label uniquely identifying each generator is also printed and applied to each bucket. A hood is then applied to each bucket. A handle is then applied to each hood.

The system 10 may generally include any suitable transport systems and devices to facilitate transferring column assemblies between stations. In some embodiments, for example, each of the stations includes at least one telemanipulator to allow an operator outside the hot cell environment (i.e., within the surrounding room or lab) to manipulate and transfer column assemblies within the hot cell environment. Moreover, in some embodiments, the system 10 includes a conveyance system to automatically transport column assemblies between the stations and/or between substations within one or more of the stations (e.g., between a fill substation and a wash substation within the fill/wash station 18).

In the example embodiment, some stations of the system 10 include and/or are enclosed within a shielded nuclear radiation containment chamber, also referred to herein as a "hot cell". Hot cells generally include an enclosure 11 constructed of nuclear radiation shielding material designed to shield the surrounding environment from nuclear radiation. Suitable shielding materials from which hot cells may be constructed include, for example and without limitation, lead, depleted uranium, and tungsten. In some embodiments, hot cells are constructed of steel-clad lead walls forming a cuboid or rectangular prism. In some embodiments, a hot cell may include a viewing window constructed of a transparent shielding material. Suitable materials from which viewing windows may be constructed include, for example and without limitation, lead glass. In the example embodiment, each of the cask loading station 12, the formulation station 14, the fill/wash station 18, the assay/autoclave loading station 20, the autoclave station, the autoclave unloading station 24, and the shielding station 28 include and/or are enclosed within a hot cell.

In some embodiments, one or more of the stations are maintained at a certain clean room grade (e.g., Grade B or Grade C). In the example embodiment, pre-autoclave hot cells (i.e., the cask loading station 12, the formulation station 14, the fill/wash station 18, the assay/autoclave loading station 20) are maintained at a Grade C clean room environment, and the autoclave unloading cell or station 24 is maintained at a Grade B clean room environment. The shielding station 28 is maintained at a Grade C clean room environment. The packaging station 30 is maintained at a Grade D clean room environment.

Additionally, the pressure within one or more stations of the system 10 may be controlled at a negative or positive pressure differential relative to the surrounding environment and/or relative to adjacent cells or stations. In some embodiments, for example, all hot cells are maintained at a negative pressure relative to the surrounding environment. Moreover, in some embodiments, the isolator of the quality control testing station 26 is maintained at a positive pressure relative to the surrounding environment and/or relative to adjacent stations of the system 10 (e.g., relative to the autoclave unloading station 24).

In this embodiment, the system 10 includes liquid handling systems for handling liquids quickly, accurately, and precisely. At least some of the liquid handling systems are disposed in the hot cells and/or handle radioactive liquids. Accordingly, the liquid handling systems may withstand radiation that would harm people and most electronic equipment. For example, the liquid handling systems may handle a Molybdenum-99 (Mo-99) solution which may deliver a lethal radiation dose in less than 5 minutes to an unprotected observer standing approximately 12 inches away. In other words, operators in the area of the Mo-99 solution would be exposed to a field equal to 5.4 Million millirem per hour (mREM/hr), or 54,000 times greater than the Nuclear Regulatory Commission standard for a high radiation area. As used throughout this disclosure, the term "high radiation area" refers to an area in which radiation levels exceed 100 mREM/hr at 30 centimeters from the radiation source.

The described liquid handling systems withstand the relatively high radiation doses in the high radiation area with minimal deterioration. Moreover, the liquid handling systems are unshielded to reduce the amount of space occupied by the liquid handling systems. The liquid handling systems may be used to transport any liquids, including radioactive and nonradioactive materials. For example, the liquid handling systems may dispense high radioactive pharmaceutical liquids such as clean injectable solutions. At least some of the liquid handling systems automatically dispense the liquids. In alternative embodiments, the system 10 may include any liquid handling systems that enable the system 10 to operate as described.

Figure 2:
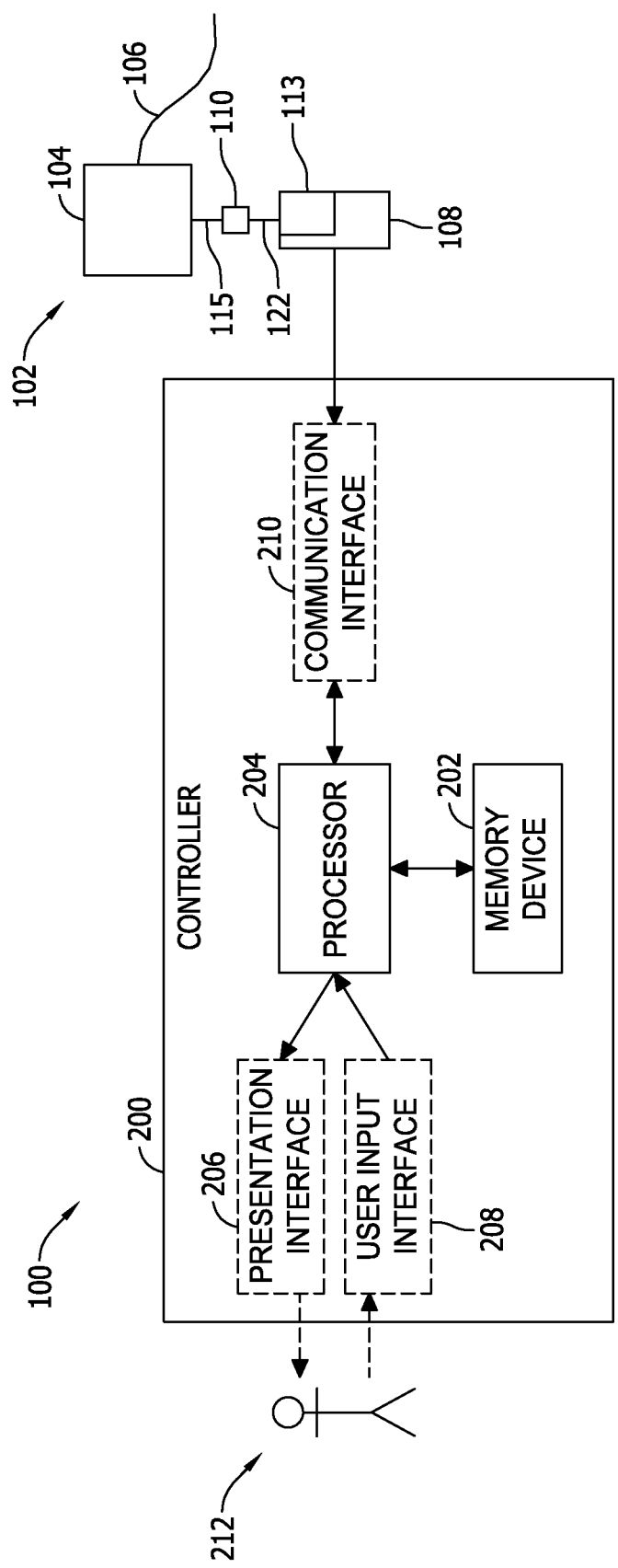
FIG. 2 is a schematic view of a fluid handling system.

FIG. 2 is a schematic view of a liquid handling system 100 for use with the system 10. In this embodiment, the liquid handling system 100 includes at least one positive displacement pump 102, or more specifically, a peristaltic pump, and a controller 200. Each pump 102 includes a pump head 104, tubing 106, a servomotor 108 with power and feedback cabling, and a coupling 110 connecting the pump head to the servomotor.

Figure 3:
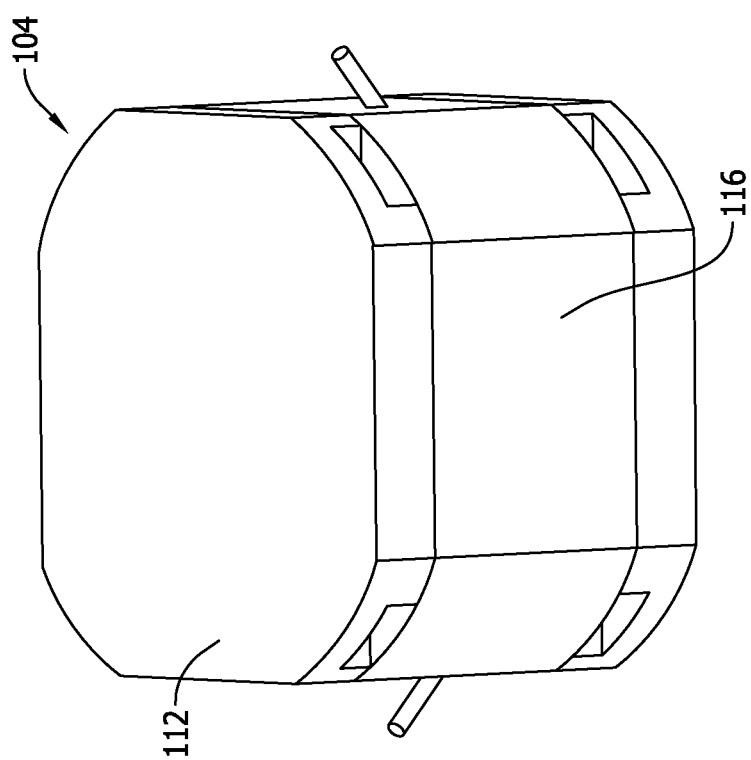
FIG. 3 is an isometric view of a pump head of the fluid handling system shown in FIG. 2.
Figure 4:
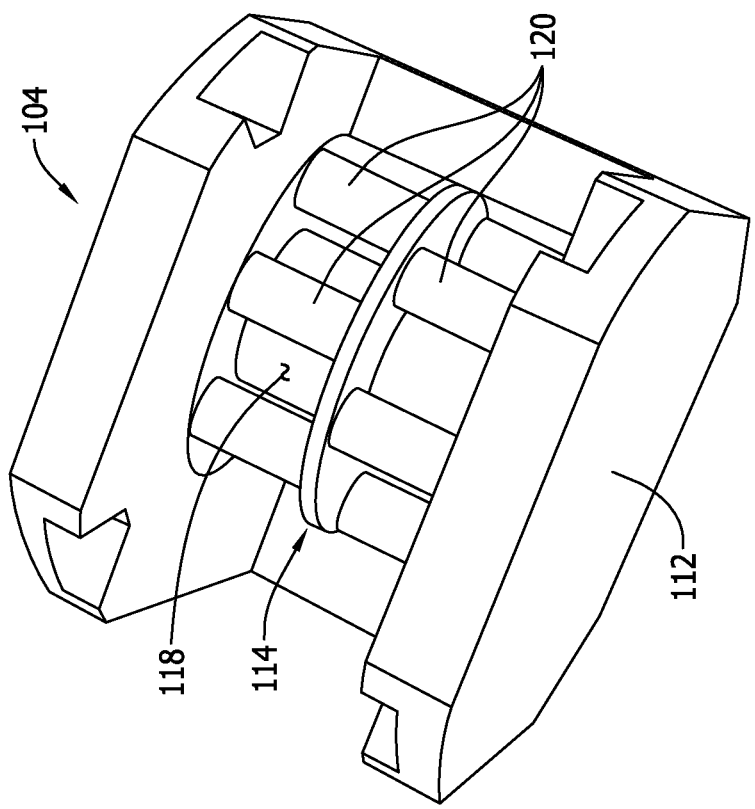
FIG. 4 is an isometric view of the pump head with a head clamp removed to show a rotor of the pump head.

In reference to FIGS. 2, 3 and 4, the pump head 104 includes a casing 112, a rotor 114 with a keyed shaft 115, and a head clamp 116. The casing 112 defines an interior space 118 and at least partially encloses the rotor 114. The head clamp 116 compresses tubing 106 against the rotor 114. The rotor 114 rotates in relation to the casing 112 within the interior space 118. The servomotor 108 controls the rotation of the rotor 114 and transmits signals relating to the rotation of the rotor. One example of a suitable pump head is a FLEXICON pump head available from WATSON-MARLOW, INC.

The tubing 106 generally extends through the pump head 104 and transports fluid through the pump 102. The rotor 114 includes a plurality of rotor heads 120 that are spaced from the head clamp 116 a distance less than the outer diameter of the tubing 106. The tubing 106 is compressed between the rotor heads 120 and the head clamp 116. The rotor heads 120 move along the tubing 106 as the rotor 114 rotates. As a result, fluid in the tubing 106 is directed through the pump head 104 as the rotor 114 rotates. Accordingly, in this embodiment the pump 102 is a peristaltic pump. In alternative embodiments, the liquid handling system may include any pumps that enable the liquid handling system to function as described.

For example, the pump 102 may dispense fluids at a speed of approximately 12 milliliters per second (mLs/sec) using 3.2 millimeter (mm) ID-tubing. The pump 102 of this embodiment dispenses liquids without the use of a nozzle. The volume of liquid dispensed may be in range of about 2.5 milliliters (mLs) to about 60 mLs. The accuracy limitations may depend on the size and type of the tubing 106. For example, a smaller ID tubing may allow greater accuracy for smaller dispense volumes. In this embodiment, the tubing 106 is made of silicone. Accordingly, the tubing 106 may be removed and replaced to eliminate cross-contamination between batches, and to remove radioactively contaminated consumables from the area. In alternative embodiments, the liquid handling systems may include any tubing that enables the liquid handling systems to operate as described.

The liquid handling system 100 is able to withstand high levels of radiation. For example, the pump head 104, shafts, couplings, motors, feedback mechanisms, and cabling are able to withstand high levels of radiation. Electrical cabling is insulated using materials, such as polyurethane, that are suitable to withstand high levels of radiation.

In reference to FIG. 2, in this embodiment, a zero-backlash coupling 110 is positioned between the pump head 104 and the servomotor 108, keyed at the pump head shaft 115 and the motor shaft 122. Accordingly, the keyed coupling 110 eliminates backlash between the pump head 104 and rotor 114. In alternative embodiments, the liquid handling system may include any coupling 110 that enables the liquid handling system to function as described.

The servomotor 108 and pump head 104 are connected by the shafts 115, 122 and coupling 110. The shafts 115, 122, and the coupling 110 allow the servomotor 108 to be spaced from the pump head 104 and prevent backlash. In particular, the shaft 115 extends from the pump head 104 towards the servomotor. The shaft 122 extends from the servomotor 108 towards the pump head 104. The coupling 110 connects the shaft 115 and the shaft 122. At least one of the shafts 115, 122 is keyed to engage the keyed coupling 110 and prevent backlash during rotation of the rotor 114. In this embodiment, all of the shafts 115 and 122 are keyed to prevent the coupling moving relative axially, i.e., slipping, during operation of the pumps 102.

During operation, the servomotor 108 rotates the shaft 122 which causes the coupling 110 and the shaft 115 to rotate. The shaft 115 is coupled to the rotor 114 (shown in FIG. 4) such that rotation of the shaft 115 causes the rotor 114 to rotate. In alternative embodiments, the servomotor 108 and the pump head 104 may be connected in any manner that enables the pump 102 to operate as described.

In some embodiments, the pump head 104 and servomotor 108 are spaced apart and connected by the shafts 115, 122 and a plurality of couplings 110. In further embodiments, the shafts 115, 122 and/or couplings 110 are angled to allow the pump head 104 and servomotor 108 to be spaced apart in more than one direction. In addition, the pump head 104 can be segregated and sealed in a clean environment for aseptic dispensing and sanitization, without exposing clean production areas to pump control hardware. In some embodiments, the pump head 104 is a pharmaceutical-grade pump head. As used herein, the term "pharmaceutical-grade" refers to equipment that is fabricated from non-oxidizing materials and withstands sanitization. In addition, pharmaceutical-grade equipment does not have recessed or pointed surfaces. For example, pharmaceutical-grade equipment may be manufactured from 316 gauge stainless steel and include rounded corners and flush surfaces.

The servomotor may be a servomotor 108 controlled by a programmable logic controller (PLC) to allow highly accurate and repeatable motion control. In addition, the servomotor 108 may be an AC servomotor with resolver feedback. In alternative embodiments, the pump 102 may include any servomotors that enable the fluid application system to operate as described.

The servomotor 108 can control pump head acceleration, deceleration, speed, and/or motion profile. For example, the servomotor 108 can control acceleration of the rotor 114 (shown in FIG. 4) from a stopped position. In addition, the servomotor can maintain the rotor 114 at a steady state speed and can control deceleration of the rotor. Moreover, the servomotor 108 can provide a desired motion profile including trapezoidal (linear ramp velocities) or S-curve (linear acceleration/deceleration). The relatively high torque capacity of the servomotor 108 and resolver-based feedback reduces stalling and slipping from commanded motion profiles. For example, the servomotor 108 is suitably a high torque servomotor, such as a 480 volts of alternating current (3-phase) Servomotor with fine continuous resolver-based feedback. The coupling 110 between the servomotor 108 and the pump head 104 eliminates slippage and error due to the rotational inertia of the motor or pump head. High torque allows the servomotor 108 to overcome rotor resistance against liquid-filled tubing. The pump head 104 rotation and any other motion parameters may be controlled via one logic instruction.

The servomotor 108 is equipped with a resolver-based feedback mechanism that is radiation-tolerant. A resolver 113 continuously tracks rotation of the rotor. In this embodiment, the resolver is magnetic. Accordingly, the servomotor 108 withstands the radioactive environment better than other servomotors that may include optical encoders and may deteriorate and fail in radioactive environments. For example, encoders include optics and electronics that do not withstand a high radiation environment without complete radiation shielding. In contrast to such systems, in this embodiment, the servomotor 108 does not include an encoder and/or electronic equipment that do not withstand radioactive environments. The servomotor 108 includes the resolver 113 that withstands the high radiation environment and does not require complete radiation shielding. In alternative embodiments, the servomotor 108 may include any resolver that enables the servomotor to operate as described. In further embodiments, the resolver 113 is omitted.

The resolver 113 may provide feedback of at least about 200,000 steps per 360-degree revolution of the rotor 114 (shown in FIG. 3). Accordingly, the servomotor 108 may compare planned rotational movement to actual rotational movement for $1/200,000^{th}$ of a revolution while following a specific start-to-end motion profile. If rotation of the rotor 114 is interrupted for any reason (e.g. power loss, servo drive fault, etc.), the pump 102 is able to accurately recover and complete the original dispense because the resolver 113 automatically tracks exactly what portion of the original motion was completed, and what portion remains.

Embodiments of the servomotor 108 (including the integrated resolver 113) were tested by exposing the servomotors to 400 kilograys of ionizing radiation from a Cobalt-60 (Co-60) source. The Co-60 source provided an equivalent of 40 Million REMs gamma radiation exposure. The servomotor 108 was bench-tested before and after irradiation. Bench-testing results did not indicate a degradation of performance after irradiation. The tested exposure of 400 kilograys of radiation represents 20 years of expected Mo-99 radiation exposure at an unshielded worst-case proximity.

The pumps 102 may be used to dispense non-radioactive fluid and/or radioactive fluid inside and outside of the hot cell. For example, the pumps 102 may dispense acetic acid, purified water for injection, and/or any other liquids. The liquids may be used to activate a material in column assemblies, to wash column assemblies, and/or to test column assemblies. Accordingly, the pumps may be included in any cells of the system 10 such as an activation cell, a formulation cell, a fill cell, a wash cell, and an assay cell.

In reference to FIG. 2, the controller 200 includes at least one memory device 202 and a processor 204 that is coupled to the memory device 202 for executing instructions. In this embodiment, executable instructions are stored in the memory device 202, and the controller 200 performs one or more operations described herein by programming the processor 204. For example, the processor 204 may be programmed by encoding an operation as one or more executable instructions and by providing the executable instructions in the memory device 202.

The processor 204 may include one or more processing units (e.g., in a multi-core configuration). Further, the processor 204 may be implemented using one or more heterogeneous processor systems in which a main processor is present with secondary processors on a single chip. As another illustrative example, the processor 204 may be a symmetric multi-processor system containing multiple processors of the same type. Further, the processor 204 may be implemented using any suitable programmable circuit including one or more systems and microcontrollers, microprocessors, programmable logic controllers (PLCs), reduced instruction set circuits (RISC), application specific integrated circuits (ASIC), programmable logic circuits, field programmable gate arrays (FPGA), and any other circuit capable of executing the functions described herein. In this embodiment, the processor 204 controls operation of the fluid handling systems by outputting control signals to components of the fluid handling system. Further, in this embodiment, the processor 204 determines a dispense volume based on program instructions and/or user inputs.

The memory device 202 is one or more devices that enable information such as executable instructions and/or other data to be stored and retrieved. The memory device 202 may include one or more computer readable media, such as, without limitation, dynamic random access memory (DRAM), static random access memory (SRAM), a solid state disk, and/or a hard disk. The memory device 202 may be configured to store, without limitation, application source code, application object code, source code portions of interest, object code portions of interest, configuration data, execution events and/or any other type of data.

In this embodiment, the controller 200 includes a presentation interface 206 that is connected to the processor 204. The presentation interface 206 presents information, such as application source code and/or execution events, to a user 212, such as a technician or operator. For example, the presentation interface 206 may include a display adapter (not shown) that may be coupled to a display device, such as a cathode ray tube (CRT), a liquid crystal display (LCD), an organic LED (OLED) display, and/or an "electronic ink" display. The presentation interface 206 may include one or more display devices. In this embodiment, the presentation interface 206 displays the dispense and/or transfer volumes of the fluid handling system.

The controller 200 also includes a user input interface 208 in this embodiment. The user input interface 208 is connected to the processor 204 and receives input from the user 212. The user input interface 208 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of the presentation interface 206 and the user input interface 208.

In this embodiment, the controller 200 further includes a communication interface 210 connected to the processor 204. The communication interface 210 communicates with one or more remote devices, such as the servomotor 108. In this embodiment, the controller 200 is separated from the servomotor 108 and located outside of the radioactive environment. In some embodiments, at least a portion of the controller 200 may be integrated with the servomotor 108. In alternative embodiments, the controller 200 may include any component that enables the fluid handling system to operate as described.

Figure 5:
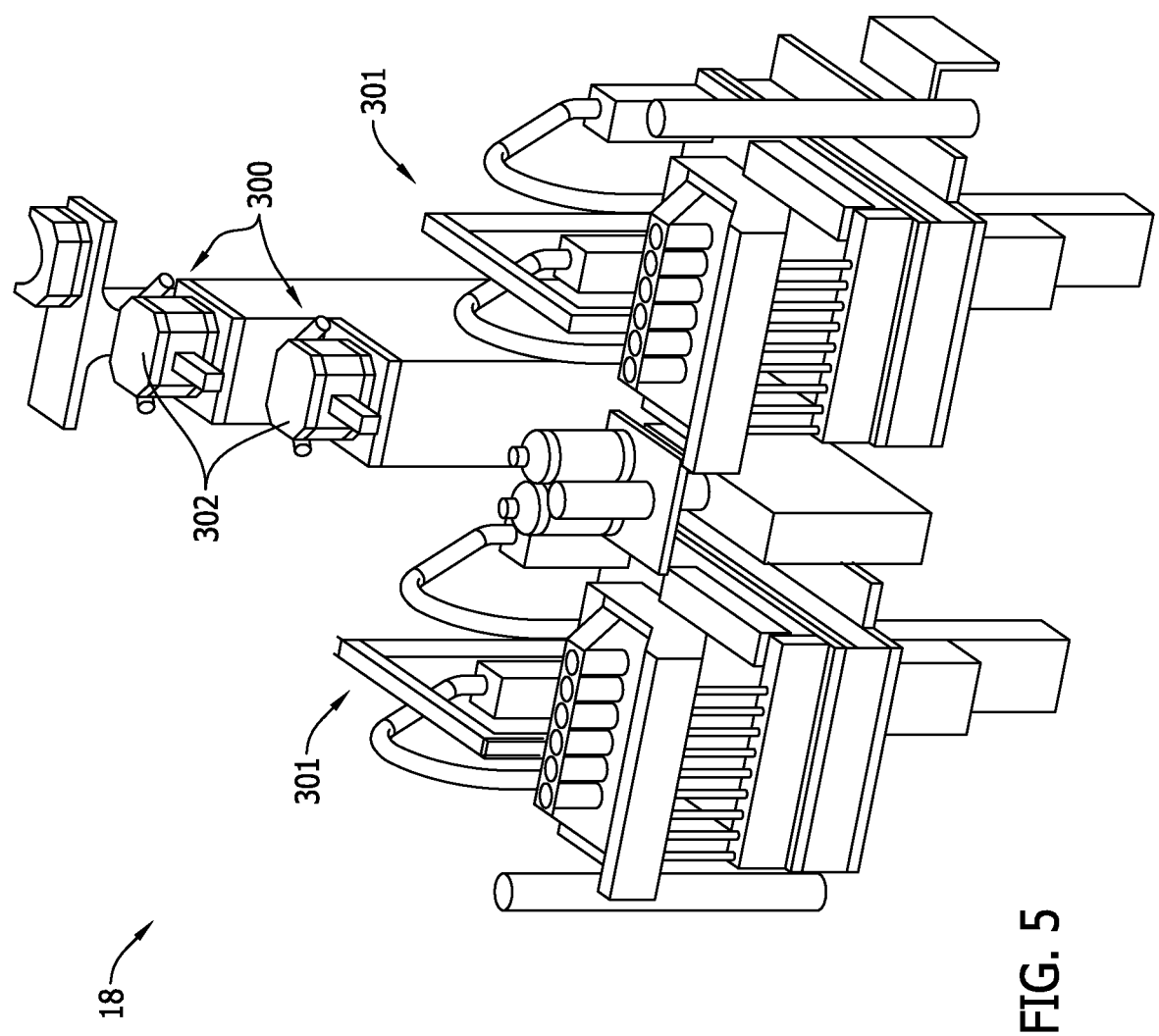
FIG. 5 is an isometric view of two dispense stations of the system shown in FIG. 1.
Figure 6:
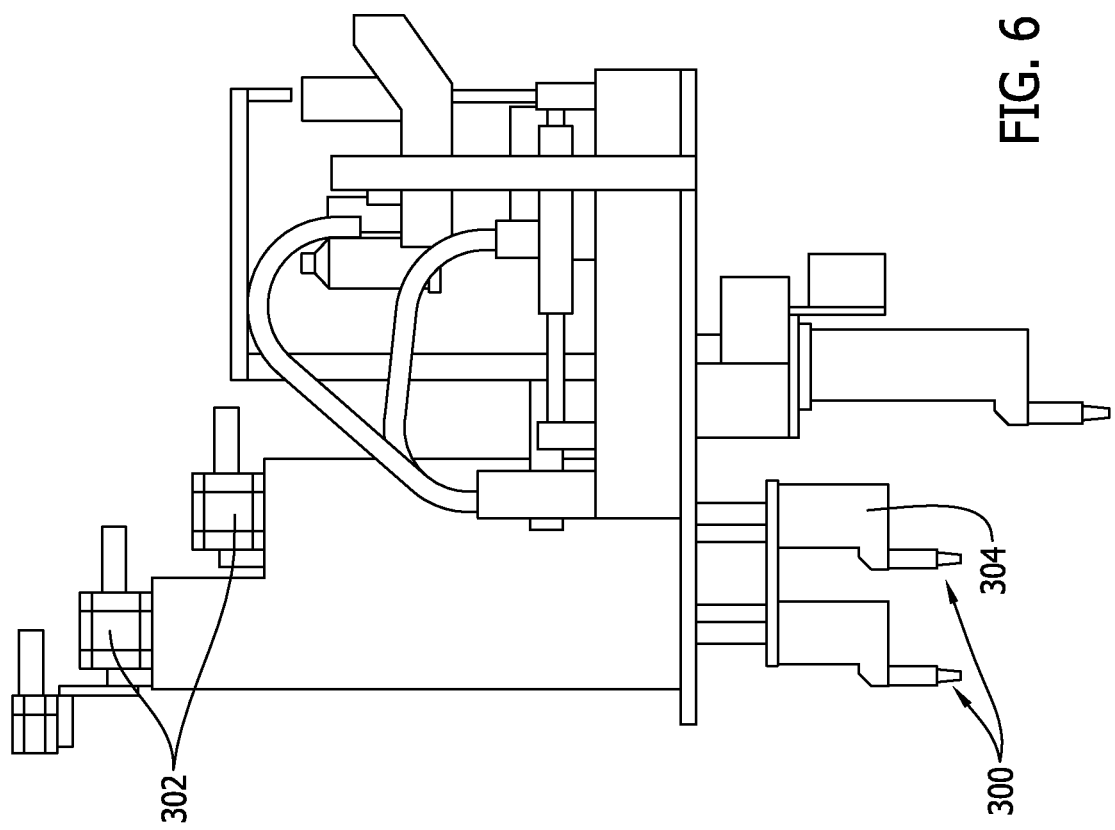
FIG. 6 is a side view of a fill station.

FIG. 5 is an isometric view of a fill station 18 of the system 10. FIG. 6 is a side view of the fill station 18. The fill station 18 includes two fill pumps 300 to dispense radioactive liquid inside the hot cells. In alternative embodiments, the fill station may include any pump that enables the system 10 to operate as described. In addition, the fill station 18 includes arms 301 that rotate and support tubing 106. The arms 301 provide consistent support to the tubing 106 and prevent binding of the tubing. In this embodiment, the fill station 18 includes two arms 301, one for each dispensing station. In alternative embodiments, the fill station 18 may include any components that enable the fill station to operate as described.

The fill pumps 300 may be used to dispense any nonradioactive and radioactive fluids. In this embodiment, the fill pumps 300 dispense Mo-99 into the column assemblies. The fill pumps 300 dispense an accurate and precise amount of the radioactive liquid into the column assemblies within very strict tolerances. For example, the fill pumps 300 may achieve dispense tolerances better than +/−1.0% of a target volume, better than +/−0.1% of a target volume, better than +/−0.01% of a target volume, better than +/−0.001% of a target volume, and even up to +/−0.0001% of a target volume.

Figure 7:
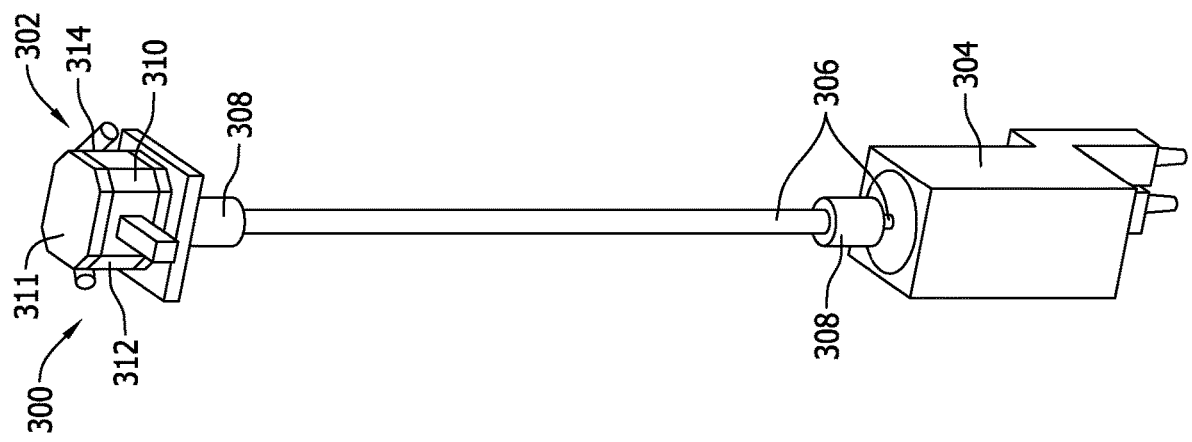
FIG. 7 is an isometric view of a dispensing pump of the fill station shown in FIG. 6.

FIG. 7 is an isometric view of one of the fill pumps 300. The fill pump 300 includes a pump head 302, a servomotor 304 with power and feedback cabling, keyed shafts 306, and keyed couplings 308. The shafts 306 and the couplings 308 extend between and connect the pump head 302 and the servomotor 304. Accordingly, the pump head 302 can be positioned in a clean processing area and the servomotor 304 can be positioned a distance from the pump head 302 to separate the servomotor from the clean processing area.

The pump head 302 includes a head clamp 310, a casing 311, a rotor, a fluid inlet 314, and a fluid outlet 312. During operation of the pump 300, fluid enters the casing 311 through the fluid inlet 314, the fluid is directed through the pump head 302 by a rotor within the pump head 302, and the fluid exits the casing 311 through the fluid outlet 312.

The keyed shafts 306 and couplings 308 allow the servomotor 304 to control rotational movement of the rotor within the pump head 302. In particular, the couplings 308 connect a middle shaft 306 to a pump head shaft 306 and a servomotor shaft 306. The couplings 308 are of zero-backlash type, and include keying features that prevent rotational slippage at the pump head shaft and at the servomotor shaft. Accordingly, the couplings 308 and the keyed shafts 306 eliminate backlash during motor and pump movement. In alternative embodiments, the pump 300 may include any couplings and shafts that enable the pump 300 to operate as described.

The servomotor 304 controls the pump head 302 and thus the dispensing of liquid. A programmable logic controller (PLC) controls an external servo drive, which controls servomotor 304, which precisely controls the pump head 302. Control is intrinsic to the PLC. Examples of control settings for the servomotor 304 are shown in the chart below.

Servomotor Settings for Dispensing a Radioactive Liquid

| Setting | Fill Low Volume | Fill High Volume |
| --- | --- | --- |
| Dispense Volume (mL) | <12.0 | >=12.0 |
| Velocity (mL/s) | 13.0 | 13.0 |
| Acceleration (mL/s2) | 20.0 | 40.0 |
| Deceleration (mL/s2) | 40.0 | 20.0 |
| Motion Profile | S-Curve | S-Curve |

Figure 8:
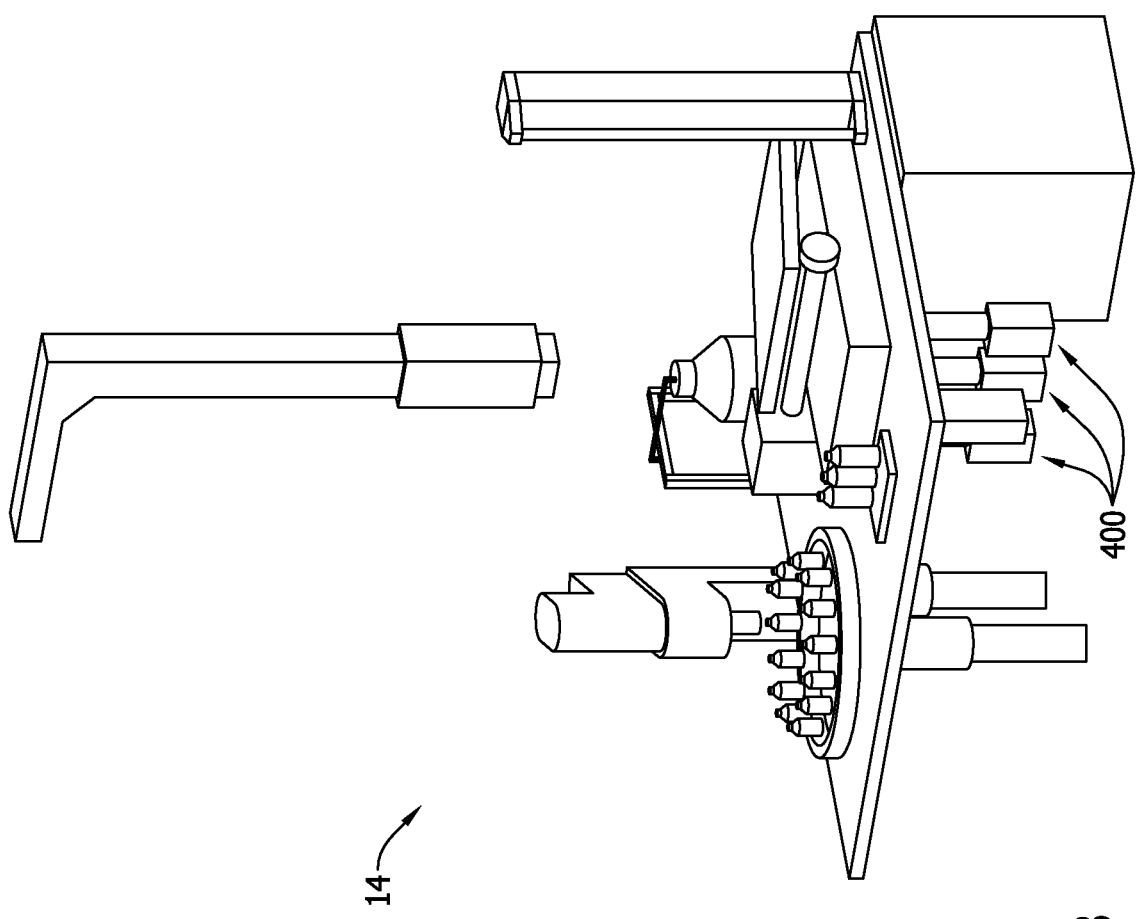
FIG. 8 is an isometric view of a formulation station of the system shown in FIG. 1.

FIG. 8 is an isometric view of a formulation station 14 of the system 10. The formulation station 14 includes three pumps 400 to transfer bulk radioactive liquid inside hot cells. For example, the bulk transfer pumps 400 may withdraw Mo-99 from shipping flasks and transfer the Mo-99 to a formulation vessel. In alternative embodiments, the formulation station 14 may include any pump that enables the formulation station to operate as described.

Figure 9:
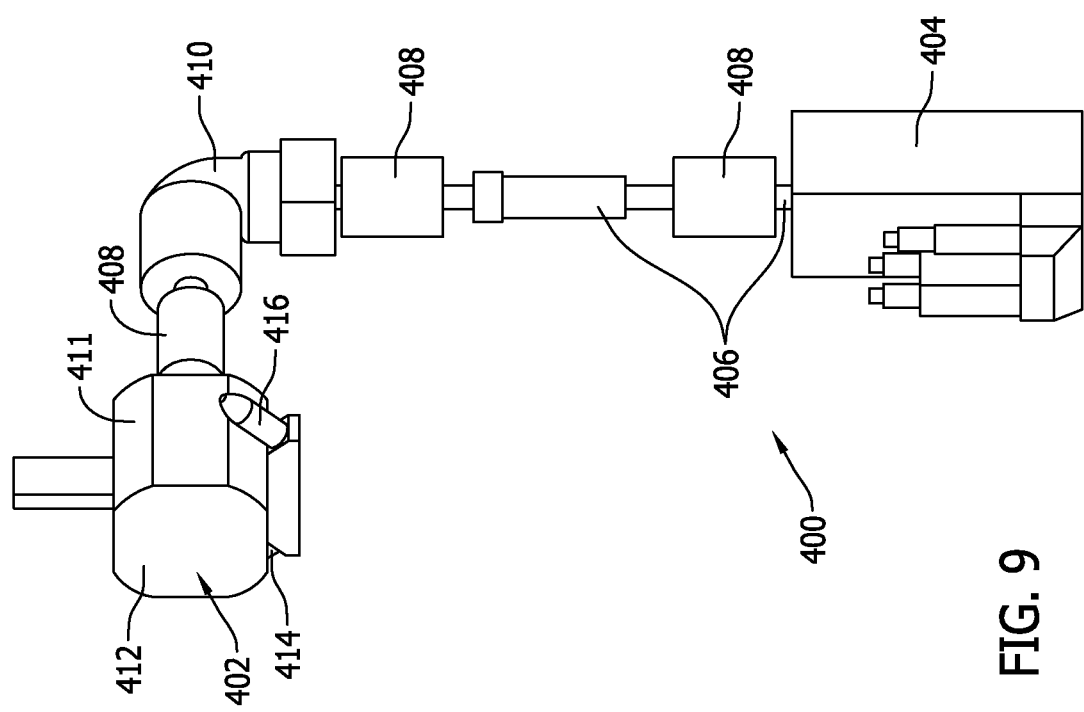
FIG. 9 is an isometric view of a pump of the formulation station shown in FIG. 8.

FIG. 9 is an isometric view of one bulk transfer pump 400 of the formulation station 14. The bulk transfer pump 400 includes a pump head 402, a servomotor 404 with feedback and power cabling, keyed shafts 406, couplings 408, and an elbow 410. The shafts 406, couplings 408, and elbow 410 extend between and connect the pump head 402 and the servomotor 404. The pump 400 includes three couplings 408. One of the couplings 408 is disposed adjacent each of the pump head 402, the elbow 410, and the servomotor 404. The elbow 410 connects the servomotor 404 to the pump head 402 such that the servomotor 404 can be spaced from the pump head 402 in at least two directions. Moreover, the couplings 408 and the elbow 410 allow the transfer pump 400 to be positioned to maximize space usage. The couplings 408 are of zero-backlash type, and include keying features that prevent rotational slippage at the pump head shaft 406 and at the motor shaft 406. The servomotor 404 is separated from the pump head 402 by a clean work table to prevent contamination of the fluid.

The pump head 402 includes a head clamp 411, a casing 412, a rotor, a fluid inlet 414, and a fluid outlet 416. During operation of the pump 400, fluid enters the casing 412 through the fluid inlet 414, the fluid is directed through the pump head 402 by a rotor within the pump head 402, and the fluid exits the casing 412 through the fluid outlet 416. The shaft allows the servomotor 404 to control rotational movement of the rotor within the pump head 402.

Figure 10:
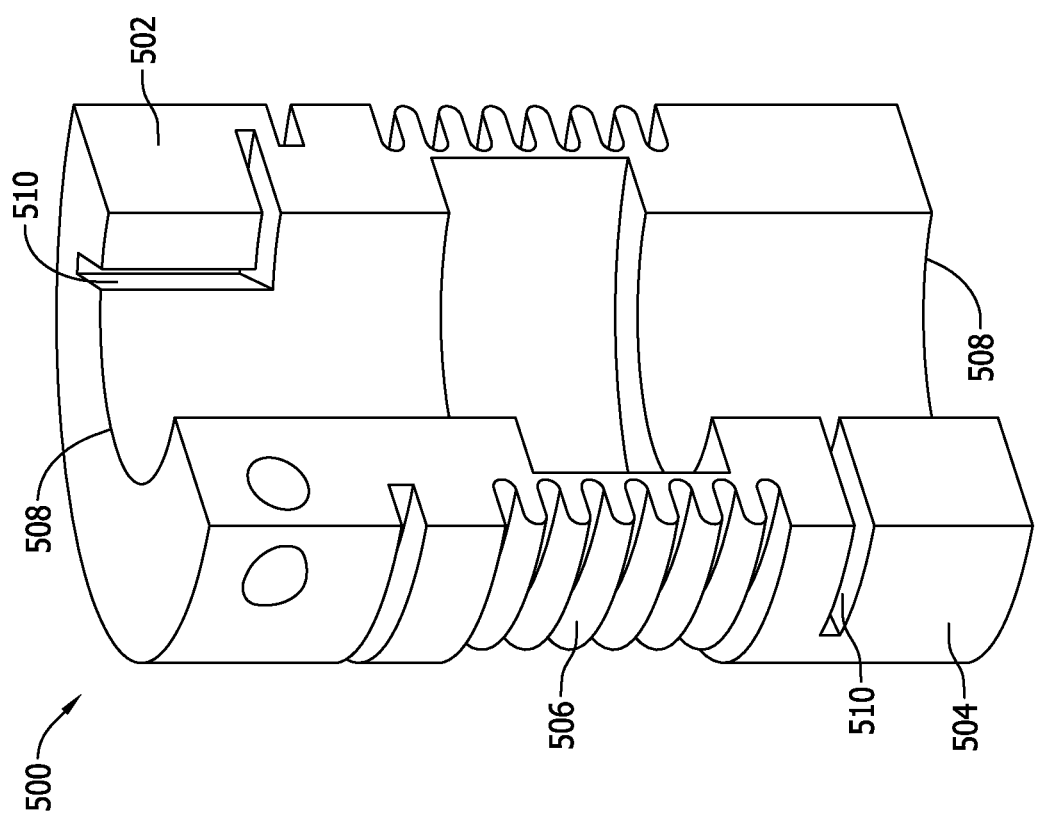
FIG. 10 is a sectional view of a coupling for use with the pumps shown in FIGS. 2, 7, and 9.

FIG. 10 is a sectional view of a coupling 500 for use with the pumps 102, 300,and 400. The coupling 500 includes a first end portion 502, a second end portion 504, and a bellows 506 extending between the first end portion and the second end portion. The first end portion 502 and the second end portion 504 include openings 508 to receive shafts. In addition, the first end portion 502 and the second end portion include a keyway 510 to engage keyed shafts. Accordingly, the coupling 500 connects shafts together and prevents backlash between the shafts. One example of a suitable coupling 500 is a Gerwah metal bellows coupling, series AKN, available from Ringfeeder Power Transmission, GMBH.

During operation, a keyed shaft is inserted into the first end portion 502 and/or the second end portion 504 of the coupling such that a key of the shaft extends into and slides along the keyway 510. The keyed shaft and/or the coupling 500 is rotated to engage the key in the keyway 510. In alternative embodiments, the coupling 500 and shaft may engage in any manner that enables the coupling 500 to function as described. For example, in some embodiments, the coupling 500 may be keyed and the shaft may include a keyway.

In this embodiment, the coupling 500 is cylindrical and extends linearly from the first end portion 502 to the second end portion 504. Accordingly, keyed shafts connected to the coupling 500 are aligned axially with each and with the coupling. In alternative embodiments, the coupling 500 may have any shape and may extend in any direction. For example, in some embodiments, the coupling 500 may be angled to connect shafts extending in different directions.

Embodiments of the systems and methods described provide several advantages over known systems. For example, embodiments of the systems and methods dispense accurate and precise volumes of nonradioactive and radioactive fluids. In addition, the fluid handling systems are not sensitive to radiation levels and can operate in radioactive environment without being shielded from the radiation. For example, the fluid handling systems include a pump head connected to a servomotor via zero-backlash keyed couplings. The control components are segregated from the pump to allow the pump to be placed within the high radiation environment without control components deteriorating due to the radiation. The servomotor provides for continuous control of the pump head and includes an integrated resolver to provide feedback from the pump head. Moreover, the fluid handling systems provide an increased pumping rate.

Embodiments of the fluid handling systems reduce contamination during processing of radioactive materials. The fluid handling systems include disposable tubing that contains radiological contamination and may be replaced after use to eliminate chemical and biological contamination between batches. Moreover, the fluid handling systems include pumps with servomotors that are separated from the clean processing area to reduce contamination. The pumps are not contaminated by the radioactive liquid and may be cleaned easily between batches. Also, the pumps are quicker than systems such as stepper-driven syringe pumps, pneumatically-driven syringe pumps, and gravimetric dispensing pumps. In addition, the pumps do not require placing objects on a scale and are usable with a broader range of materials than at least some known pumps.

When introducing elements of the present invention or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A system for manufacturing radionuclide generators, the system comprising:
    an enclosure defining a radioactive environment, the
        enclosure including radiation shielding to prevent radiation within the radioactive environment from moving to an exterior of the enclosure; and a pump within the enclosure for transferring fluid through tubing, the pump comprising:

a pump head including a casing, a rotor that rotates in relation to the casing, and a clamp, the tubing extending through the pump head, the clamp compressing the tubing against the rotor and directing radioactive fluid through the tubing as the rotor rotates;

a servomotor that controls the rotation of the rotor; and a coupling connecting the pump head to the servomotor, wherein the coupling prevents backlash between the servomotor and the rotor during rotation.

2. The system of claim 1, wherein the servomotor includes a resolver to generate signals relating to the rotation of the rotor.

3. The system of claim 1, wherein the pump further comprises cables connected to the servomotor, the cables including polyurethane insulation to resist the effects of radiation.

4. The system of claim 1, wherein the pump further comprises a first keyed shaft extending between the coupling and the rotor, wherein the first keyed shaft is engaged with the coupling.

5. The system of claim 4, wherein the pump further comprises a second keyed shaft extending between the coupling and the servomotor, wherein the second keyed shaft is engaged with the coupling.

6. The system of claim 1, wherein the coupling is a first coupling, the pump further comprising a second coupling and a shaft extending between the first coupling and the second coupling.

7. The system of claim 1, wherein the pump head is a peristaltic pump head and is positioned within a clean environment, and wherein the pump head is separated from the servomotor to prevent contamination of the fluid.

8. A pump for transferring fluid through tubing in a radioactive environment, said pump comprising:

a pump head including a casing, a rotor that rotates in relation to the casing, and a clamp, the tubing extending through the pump head, the clamp compressing the tubing against the rotor and directing radioactive fluid through the tubing as the rotor rotates, the rotor including a keyed shaft;

a servomotor that controls the rotation of the rotor and includes a magnetic resolver to generate signals relating to the rotation of the rotor; and a coupling connecting the pump head to the servomotor, wherein the coupling is connected to the keyed shaft to prevent backlash between the servomotor and the rotor during rotation, wherein the pump and servomotor are positioned in a high radiation area.

9. The pump of claim 8, the pump further comprising cables connected to the servomotor, the cables including polyurethane insulation to resist the effects of radiation.

10. The pump of claim 8 further comprising a second keyed shaft extending between the coupling and the servomotor, wherein the second keyed shaft is connected to the coupling.

11. The pump of claim 8, wherein the coupling is a first coupling, the pump further comprising a second coupling and a shaft extending between the first coupling and the second coupling.

12. The pump of claim 8, wherein the pump head is a pharmaceutical-grade peristaltic pump head.

13. The pump of claim 8, wherein the pump head is positioned within a clean environment and is separated from the servomotor to prevent contamination of the fluid.

14. The pump of claim 8, wherein the coupling defines a keyway to engage the keyed shaft.

15. A method of transferring fluid through tubing in a radioactive environment, the tubing extending through a pump head of a pump, the pump including a casing, a rotor that rotates in relation to the casing, and a clamp, the method comprising:

compressing the tubing against the rotor;

rotating the rotor to direct fluid through the tubing, the rotor including a keyed shaft;

controlling rotation of the rotor using a servomotor connected to the rotor by the keyed shaft and a coupling; and engaging the coupling and the keyed shaft to prevent backlash between the servomotor and the rotor during rotation, wherein the pump and servomotor are positioned in a high radiation area.

16. The method of claim 15 further comprising generating signals relating to the rotation of the rotor using a resolver of the servomotor.

17. The method of claim 15 further comprising dispensing the fluid into a container, wherein the servomotor is configured to control a dispense volume of the fluid.

18. The method of claim 15, the method further comprising supplying power to the servomotor through cables connected to the servomotor, the cables including polyurethane insulation to resist the effects of radiation.

19. The method of claim 15 further comprising engaging the coupling and a second keyed shaft extending between the coupling and the servomotor.

20. The method of claim 15 further comprising rotating the keyed shaft and the coupling to cause rotation of the rotor.

* * * * *